United States Patent
Karnofsky

(10) Patent No.: US 11,938,012 B1
(45) Date of Patent: Mar. 26, 2024

(54) DEVICES AND METHODS FOR DISPENSING BANDAGES

(71) Applicant: Glenn Karnofsky, Kings Beach, CA (US)

(72) Inventor: Glenn Karnofsky, Kings Beach, CA (US)

( * ) Notice: Subject to any disclaimer, the term of this patent is extended or adjusted under 35 U.S.C. 154(b) by 0 days.

(21) Appl. No.: 18/094,158

(22) Filed: Jan. 6, 2023

(51) Int. Cl.
*A61F 15/00* (2006.01)

(52) U.S. Cl.
CPC .................................. *A61F 15/002* (2013.01)

(58) Field of Classification Search
CPC ........ A61F 15/002; A61F 13/02; A61F 15/00; B65D 83/08; B65D 75/32; A47F 5/08
USPC ............. 221/72; 211/113; 206/390, 441, 460
See application file for complete search history.

(56) References Cited

U.S. PATENT DOCUMENTS

| | | | | | |
|---|---|---|---|---|---|
| 2,133,609 | A | * | 10/1938 | Eustis ................. | A61F 13/0203 602/42 |
| 2,338,041 | A | * | 12/1943 | King .................. | B65D 85/1027 206/264 |
| 2,708,030 | A | * | 5/1955 | Newton ............... | B65D 85/672 225/89 |
| 3,051,584 | A | * | 8/1962 | Tindall ................ | B65D 5/4204 206/820 |
| 3,420,405 | A | * | 1/1969 | Taylor ................. | B65D 83/08 206/215 |
| 3,520,403 | A | * | 7/1970 | Moshel ............... | A61F 15/001 221/87 |
| 3,835,992 | A | * | 9/1974 | Adams, IV .......... | B65D 83/0835 206/390 |
| 4,194,624 | A | * | 3/1980 | Spiegelberg .......... | B65D 83/08 206/441 |
| 4,355,720 | A | * | 10/1982 | Hofberg .............. | B65D 71/00 206/460 |
| 5,271,522 | A | * | 12/1993 | Ko ..................... | A61F 15/001 221/46 |
| 5,358,140 | A | * | 10/1994 | Pellegrino ........... | A61F 15/001 206/440 |

(Continued)

FOREIGN PATENT DOCUMENTS

| | | | | |
|---|---|---|---|---|
| EP | 3669846 | A1 * | 6/2020 | ........... A61F 15/001 |
| WO | WO-03060843 | A1 * | 7/2003 | ........... A61F 15/001 |

(Continued)

*Primary Examiner* — Rakesh Kumar
(74) *Attorney, Agent, or Firm* — Haley Guiliano LLP

(57) ABSTRACT

A method and device for dispensing bandages is disclosed. The method and device may include an exterior enclosing an interior of the bandage dispensing device, a dispensing port, and a bandage carriage located within the interior of the device. In some embodiments, the device may further include a first bandage of a plurality of bandages, each having a first end and a second end, the bandage carriage having a plurality of bandage slots, and the second end of the first bandage extends through a first bandage slot of the plurality of bandage slots. A method for dispensing bandages is also disclosed. In an embodiment, pulling a first end of a first bandage of a plurality of bandages that protrudes through a dispensing port, a second end of the first bandage of the plurality of bandages is connected to a bandage carriage located in an interior of a bandage dispensing device, the bandage carriage may be configured in a generally circular shape, and a second bandage of the plurality of bandages is connected to the carriage.

7 Claims, 10 Drawing Sheets

(56) References Cited

U.S. PATENT DOCUMENTS

| | | | | |
|---|---|---|---|---|
| 5,685,833 A * | 11/1997 | Turngren | A61F 15/001 | 602/57 |
| 5,891,078 A * | 4/1999 | Turngren | A61F 13/0279 | 602/57 |
| 6,079,190 A * | 6/2000 | Simpson | B65D 75/30 | 221/60 |
| 6,092,657 A * | 7/2000 | Hopkins | B65H 35/002 | 206/397 |
| 6,394,306 B1 * | 5/2002 | Pawlo | B65D 83/0463 | 221/258 |
| 6,612,437 B1 * | 9/2003 | Klemets | B24D 11/00 | 206/445 |
| D637,299 S * | 5/2011 | Cowles | D24/189 | |
| 7,963,201 B2 * | 6/2011 | Willoughby | G07F 17/0092 | 83/210 |
| 9,751,674 B1 * | 9/2017 | Hoover | A61F 15/002 | |
| 10,264,869 B2 * | 4/2019 | Brouillet | A41G 5/02 | |
| 10,610,424 B1 * | 4/2020 | Hoover | A61F 15/002 | |
| 2002/0170918 A1 * | 11/2002 | Solovay | A61F 15/002 | 221/73 |
| 2003/0047566 A1 * | 3/2003 | DeVita | A61F 15/002 | 221/73 |
| 2004/0099626 A1 * | 5/2004 | Belt | A47F 5/0006 | 211/85.15 |
| 2004/0262250 A1 * | 12/2004 | Kosir | A47F 5/0884 | 211/113 |
| 2007/0191753 A1 * | 8/2007 | Wendorf | A61F 15/002 | 602/58 |
| 2007/0215634 A1 * | 9/2007 | Levin | A61M 5/44 | 221/231 |
| 2010/0270324 A1 * | 10/2010 | Blum | A61F 15/001 | 221/45 |
| 2012/0211507 A1 * | 8/2012 | Burns | B65D 75/366 | 221/70 |
| 2012/0292217 A1 * | 11/2012 | Grossman | A61F 15/001 | 206/441 |
| 2013/0233876 A1 * | 9/2013 | Teates | A61F 15/002 | 221/70 |
| 2013/0256171 A1 * | 10/2013 | Kerdemelidis | A61F 15/001 | 206/476 |
| 2014/0261514 A1 * | 9/2014 | Martins | A41G 5/02 | 132/201 |
| 2014/0263392 A1 * | 9/2014 | Martins | B65D 83/0864 | 221/71 |

FOREIGN PATENT DOCUMENTS

| | | | | |
|---|---|---|---|---|
| WO | WO-03063750 A1 * | 8/2003 | | A61F 13/0276 |
| WO | WO-2015004513 A1 * | 1/2015 | | A47F 5/112 |

* cited by examiner

A
DEVICES AND METHODS FOR DISPENSING BANDAGES

INTRODUCTION

The present disclosure is directed towards devices and methods for dispensing bandages and, more particularly, for dispensing bandages stored within a bandage dispensing device.

BACKGROUND

For many years, bandages have been used to dress and treat wounds. Beginning with simple cloth materials, bandage technology has progressed to include features that make them easy to use and apply while maintaining their sterility during storage. For example, bandages are widely available that are individually packaged such that the packaging can be peeled back to reveal the bandage. In such embodiments, bandages typically have peelable backing that protects the bandage's adhesive portion. To apply such bandages, a user must first remove the individually packaged bandage, usually from a box, bag, or some other storage device. Then, the user must remove the bandage from the packaging, usually accomplished by peeling away the packaging. Then, a user must remove the bandage backers to reveal the adhesive portions of the bandage. Only then can a user apply the bandage to the wound area to dress the injury. This process is very cumbersome, even for someone that is not injured but is instead applying the bandage to a patient. When the user is also the patient in need of the bandage, the complexity of retrieving and applying the bandage increases exponentially. This is typically due to elevated stress levels induced by the injury for which the user needs the bandage. Moreover, often times the user-patient may only be able to use one hand to retrieve and apply the bandage. For example, a user-patient may have a cut on his or her hand that requires a bandage and, in such a situation, the user-patient may not be able to use the injured hand in retrieving, preparing, and applying the bandage to the injury. Additionally, the user-patient may have blood or other fluids stemming from the wound contaminating the wound site, further inhibiting the use and application of a bandage. Therefore, what is needed is a bandage dispensing device that allows a user to easily retrieve, prepare, and apply a bandage to a wound site. This need has heretofore remained unmet.

SUMMARY

In an exemplary embodiment, the present disclosure is directed to a device for dispensing bandages. The device includes an exterior enclosing an interior of the bandage dispensing device, a dispensing port, and a bandage carriage located within the interior of the device.

In other embodiments, the device further includes a first bandage of a plurality of bandages, each having a first end and a second end. In some embodiments, the bandage carriage includes a plurality of bandage slots, the second end of the first bandage extends through a first bandage slot of the plurality of bandage slots.

In other embodiments, each bandage of the plurality of bandages includes an adhesive backer, and in some embodiments, the adhesive backer is connected to the bandage carriage.

In other embodiments, the device further includes a guide located in the interior. In some embodiments, the bandage carriage comprises a generally circular shape, and circumscribes a portion of the interior of the device corresponding to a circumference of the bandage carriage.

In other embodiments, the bandage carriage includes a plurality of bandages, each bandage of the plurality of bandages having a first end and second end. In some embodiments, the second end of a first bandage is connected to the first end of a second bandage. In this way, each bandage of the plurality of bandages are connected together to form a series of bandages.

In some embodiments, the first bandage is connected to the second bandage via a connector. In some embodiments, the connector is attached to the adhesive backer.

In some embodiments, the bandage dispensing device further includes a port cover. In some embodiments, the bandage dispensing device further includes a dust guard.

In some embodiments, device of further includes a spring, a conveyer, and a switch. In some embodiments, the spring is configured to apply a force to the bandages in the direction of the conveyer.

In other embodiments, the device further includes control circuitry operatively connected to the conveyor and the switch.

In other embodiments, the device further includes a display screen. In some embodiments, the display screen is interactive.

In other embodiments, device further includes a follower to which the force is applied.

In another exemplary embodiment, the present disclosure is directed to a device for dispensing bandages. In some embodiments, the device includes a spool comprising a plurality of bandages. In some embodiments, each bandage of the plurality of bandages comprises a first end and second end. In some embodiments, the second end of a first bandage of the plurality of bandages is connected to the first end of a second bandage of the plurality of bandages.

In other embodiments, the first bandage of the plurality of bandages is connected to the second bandage of the plurality of bandages via a connector.

In other embodiments, each bandage of the plurality of bandages includes an adhesive backer located on the first end and second end of each bandage of the plurality of bandages. In some embodiments, the adhesive backer of the second end of the first bandage is connected to the first end of the second bandage.

In another exemplary embodiment, the present disclosure is directed to a method for dispensing bandages. In some embodiments, the method includes pulling a first end of a first bandage of a plurality of bandages. In some embodiments, the first end of the first bandage protrudes through a dispensing port. In other embodiments, a second end of the first bandage of the plurality of bandages is connected to a bandage carriage located in an interior of a bandage dispensing device. In some embodiments, the bandage carriage is configured in a generally circular shape. In some embodiments, wherein a second bandage of the plurality of bandages is connected to the carriage.

In other embodiments, the carriage includes a plurality of bandage slots, and the second end of the first bandage protrudes through a first bandage slot of the plurality of bandage slots.

In other embodiments, the second end of the first bandage of the plurality of bandages further includes an adhesive backer attached to the carriage.

BRIEF DESCRIPTION OF THE DRAWINGS

The present disclosure, in accordance with one or more various embodiments, is described in detail with reference to the following figures. The drawings are provided for purposes of illustration only and merely depict typical or example embodiments. These drawings are provided to facilitate an understanding of the concepts disclosed herein and shall not be considered limiting of the breadth, scope, or applicability of these concepts. It should be noted that for clarity and ease of illustration these drawings are not necessarily made to scale.

DETAILED DESCRIPTION

Dispensing bandages can be cumbersome and difficult for various reasons such as, for example, the user having limited mobility, which may be caused by the injury for which a bandage is needed. Such mobility issues often leave the user with an inability to properly retrieve, prepare, and apply a bandage to a wound. Additionally, clinicians may experience the need to apply dozens of bandages in a short period of time, which the traditional cumbersome process of retrieving and preparing a bandage for application requires an extended period of time. The devices and methods of the present disclosure are directed to dispensing bandages quickly and in an easy manner, and in some embodiments, singlehandedly.

Figure 1:
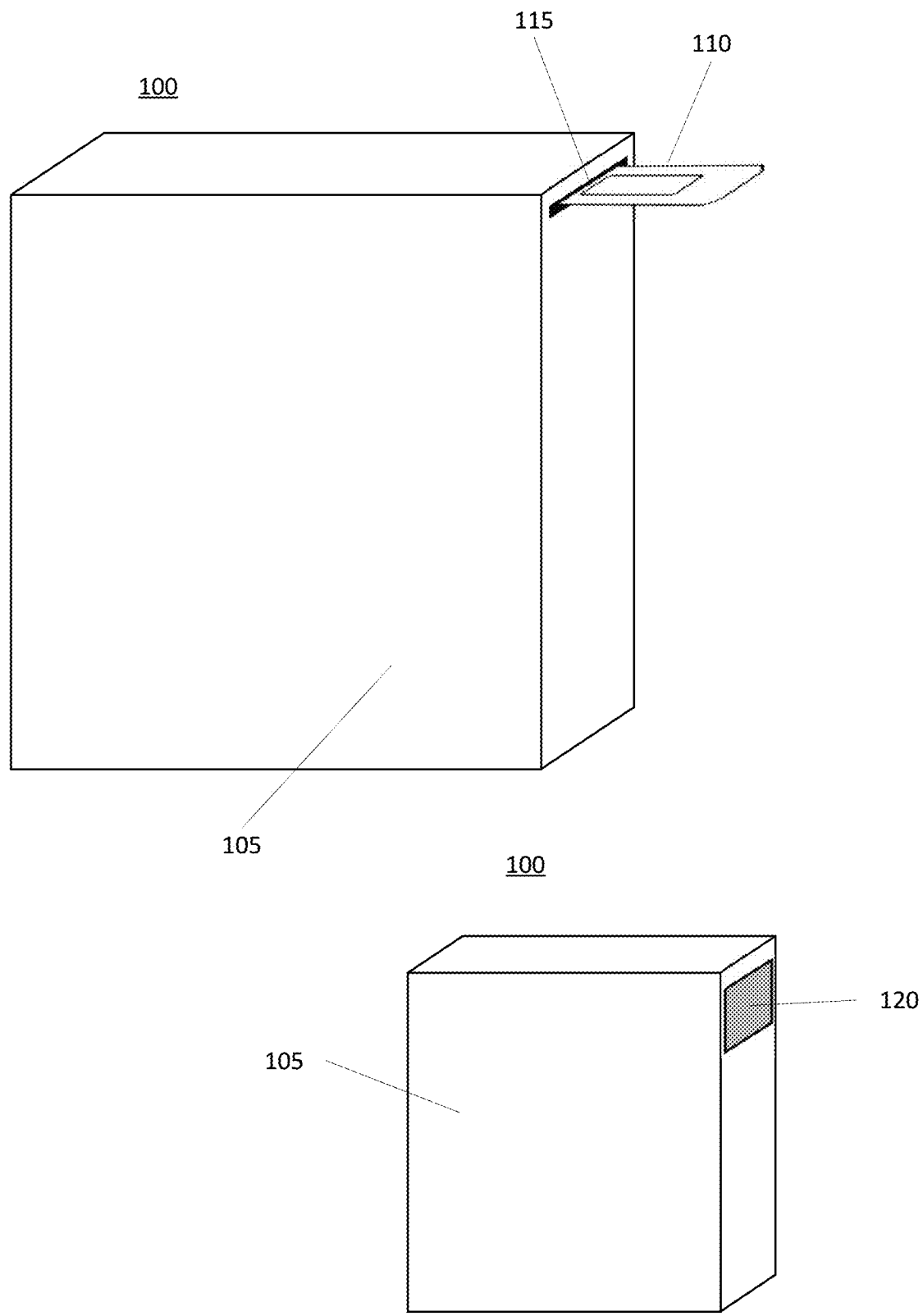
FIG. 1 illustrates an isometric view of an exemplary bandage dispensing device, in accordance with some embodiments of the present disclosure.

FIG. 1 illustrates a perspective view of a bandage dispensing device 100, in accordance with some embodiments of the present disclosure. As illustrated, bandage dispensing device 100 comprises an exterior 105 and a dispensing port 115, through which bandages 110 are dispensed. Although bandages 110 may be illustrated and described as a particular type of bandage, bandage 110 can be embodied by any type of bandage without departing from the contemplated embodiments. For example, bandage 110 may be embodied by a gauze bandage, adhesive bandage, liquid bandage, compression bandage, triangular bandage, tube bandage, or a kirigami bandage, without departing from the contemplated embodiments. Additional types of bandages include roller, triangular, four-tailed, many-tailed (Scultetus), quadrangular, elastic (elastic knit, rubber, synthetic, or a combination thereof), adhesive, elastic adhesive, cohesive bandages, impregnated bandages (plaster of Paris, waterglass (silica), starch, and any combination thereof), and stockinet. Additionally, bandage 110 may be embodied by any sanitary item, for example, menstrual pads.

In an exemplary embodiment of the present disclosure and with reference to FIG. 1, bandage dispensing device 100 comprises an exterior 105 and dispensing port 115. The exterior 105 may comprise any suitable rigid or semi-rigid material. For example, exterior 105 may be constructed from paper products such as cardboard or cardstock. Exterior 105 may be also made from polymeric material such as plastic, acrylic or polymethyl methacrylate, polycarbonate, polyethylene, polypropylene, polyethylene terephthalate, polyvinyl chloride, and acrylonitrile-butadiene-styrene (ABS). Bandages 110 may traverse dispensing port 115 from the interior of bandage dispensing device 100. In some embodiments, port cover 120 may be used to cover dispensing port 115. Port cover 120 may be made from any rigid or semi-rigid material, for example, plastic- or paper-based materials. In some embodiments, bandage dispensing device 100 comprises a dust guard that prevents dust or other contaminants from traversing to the interior of bandage dispensing device 100 while allowing a user to retrieve a bandage therefrom. In such an embodiment, the dust guard may comprise felt or other soft material that allows the dust guard to contact bandage 110 while it is being removed from bandage dispensing device 100. In other embodiments, the dust guard may further comprise bristles or some other similar materials that enable the user to retrieve a bandage 110 from bandage dispensing device 100 while preventing dust or other contaminants from entering the interior of bandage dispensing device 100. In this way, the dust guard helps maintain the sterility of bandages 110 while they are contained within bandage dispensing device 100. Although dispensing port 115 may be shown and described in a particular location relative to bandage dispensing device 100, dispensing port 115 may be located anywhere on bandage dispensing device 100. Additionally, although bandages 110 may be illustrated and described as being a particular orientations, any orientation may be implemented without departing from the contemplated embodiments.

Figure 2:
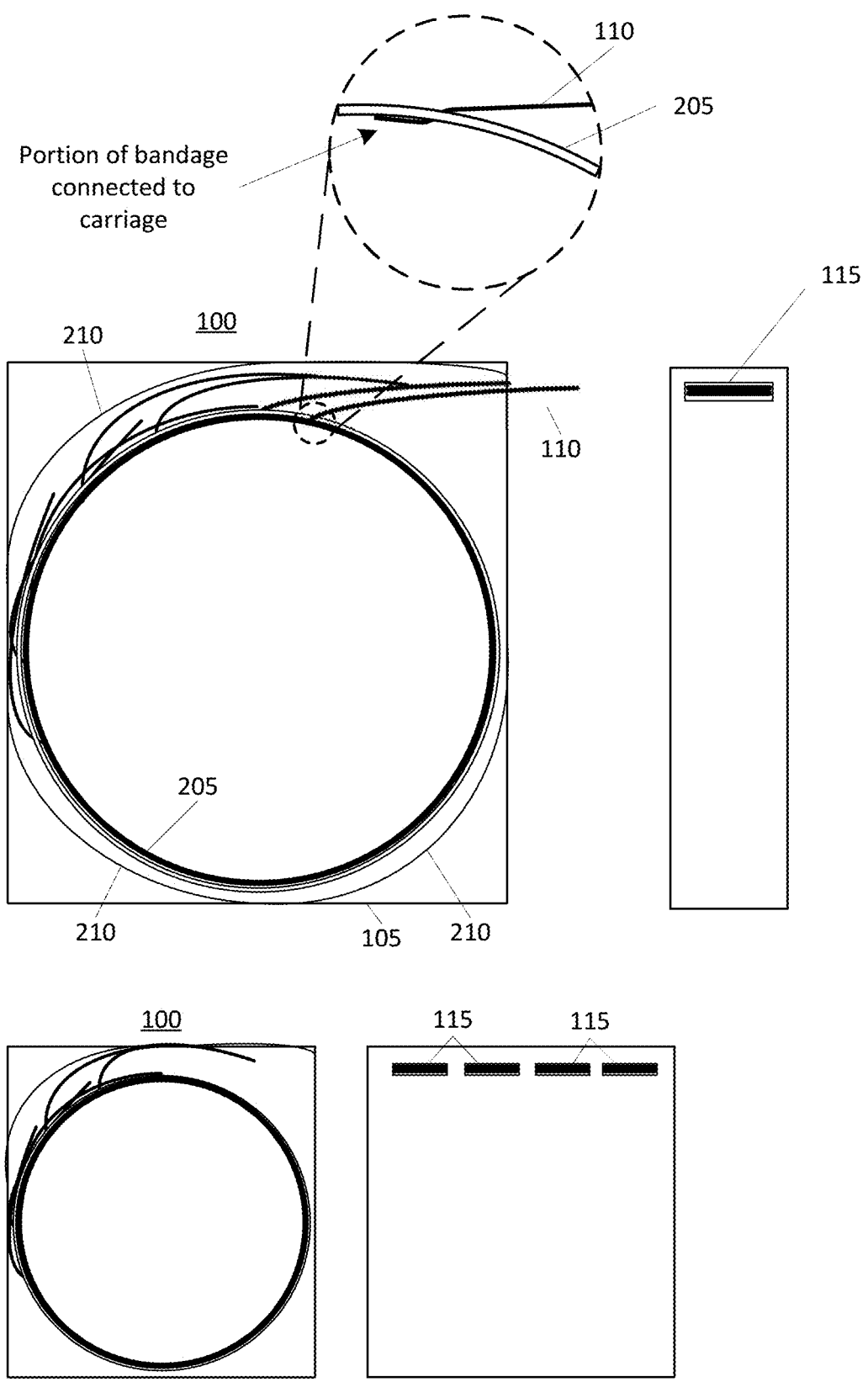
FIG. 2 illustrates perspective views and a detail view of an exemplary bandage dispensing device, in accordance with some embodiments of the present disclosure.

In another exemplary embodiment of the present disclosure and with reference to FIG. 2, bandage dispensing device 100 comprises bandage carriage 205. In some embodiments, bandage carriage 205 may be oriented in the interior or bandage dispensing device 100 such that bandage carriage 205 is able to freely rotate while located in the interior of bandage dispensing device 100. Bandage dispensing device 100 may further comprise guide 210. In operation, guide 210 prevents bandages 110 from interfering with the rotation of carriage 205. In such an embodiment, guide 210 prevents bandages 110 from being caught or tangled in the interior of bandage dispensing device 100. In this way, carriage 210 maintains bandages 110 in an orientation sufficient to allow bandages 110 be guided to port 115 while in operation. Guide 210 may comprise any suitably low friction material to allow bandages 110 to contact guide 210 yet still be able to slide while in contact with guide 210. In some embodiments, guide 210 may comprise wax paper or some other similar material. In another embodiment, bandage dispensing device 100 comprises a plurality of carriages 205. In such an embodiment, bandage dispensing may also comprise a plurality of dispensing ports 115. In such an embodiment, the plurality of carriages 205 may each comprise differing sizes and/or shapes of bandages 110. In other embodiments, the plurality of carriages 205 may comprise the same size and shape of bandages 110. FIG. 2 further illustrates a detail view of bandage 110 connected to carriage 205. As illustrated, a portion of bandage 110 protrudes through bandage carriage 205 (e.g., through bandage slot 405) and is connected to bandage carriage 205.

Figure 3:
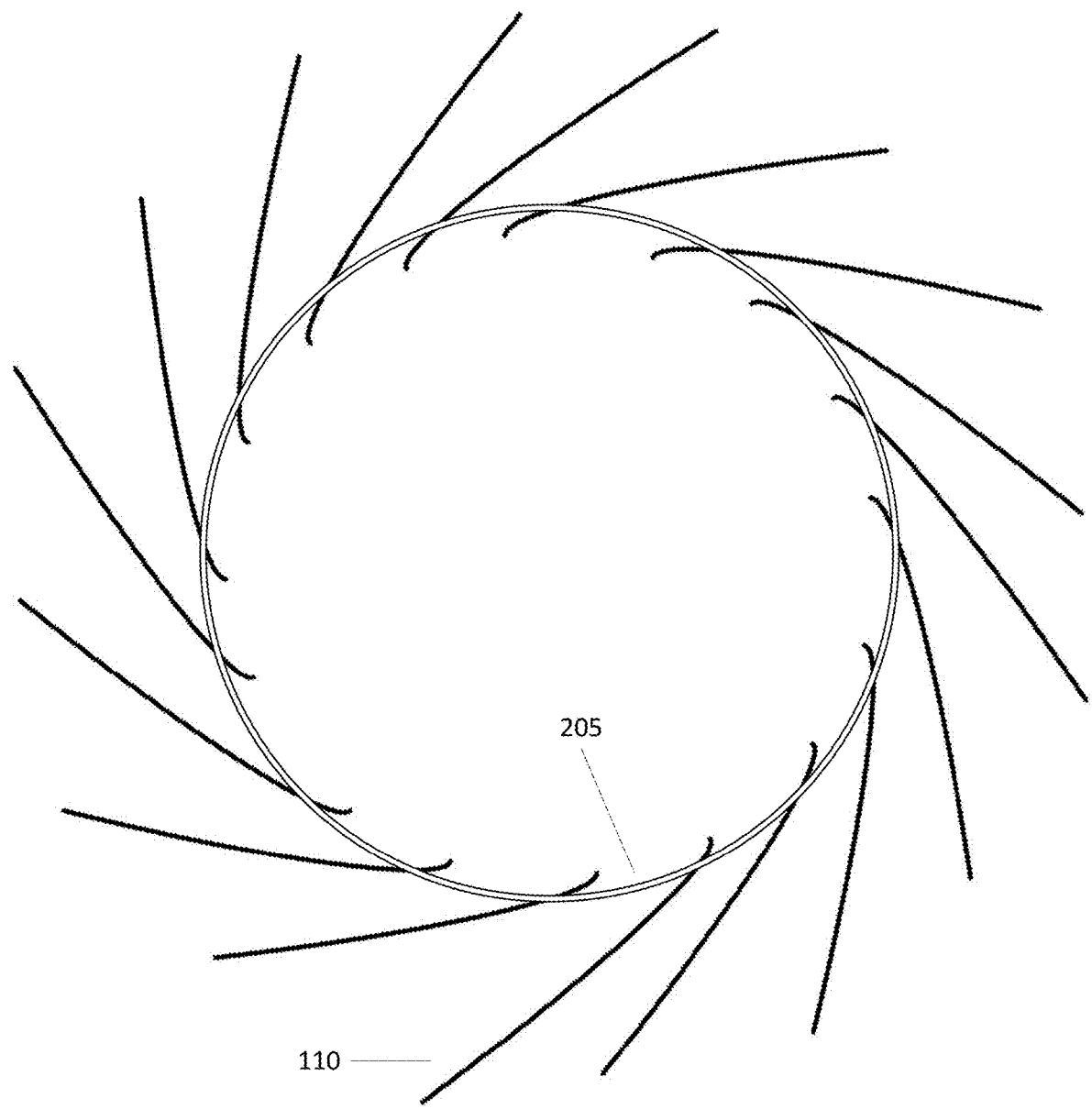
FIG. 3 illustrates a perspective view of an exemplary bandage carriage with bandages attached thereto, in accordance with some embodiments of the present disclosure.

FIG. 3 illustrates bandage carriage 205 with bandages 110 installed thereon. As depicted in FIG. 3, each bandage of the plurality of bandages 110 may be attached to carriage 205. One end of each bandage 110 may be input through bandage slot 405 such that bandages 110 protrude tangentially and/or radially from carriage 205. Any number of bandages 110 may be attached to carriage 205.

Figure 4:
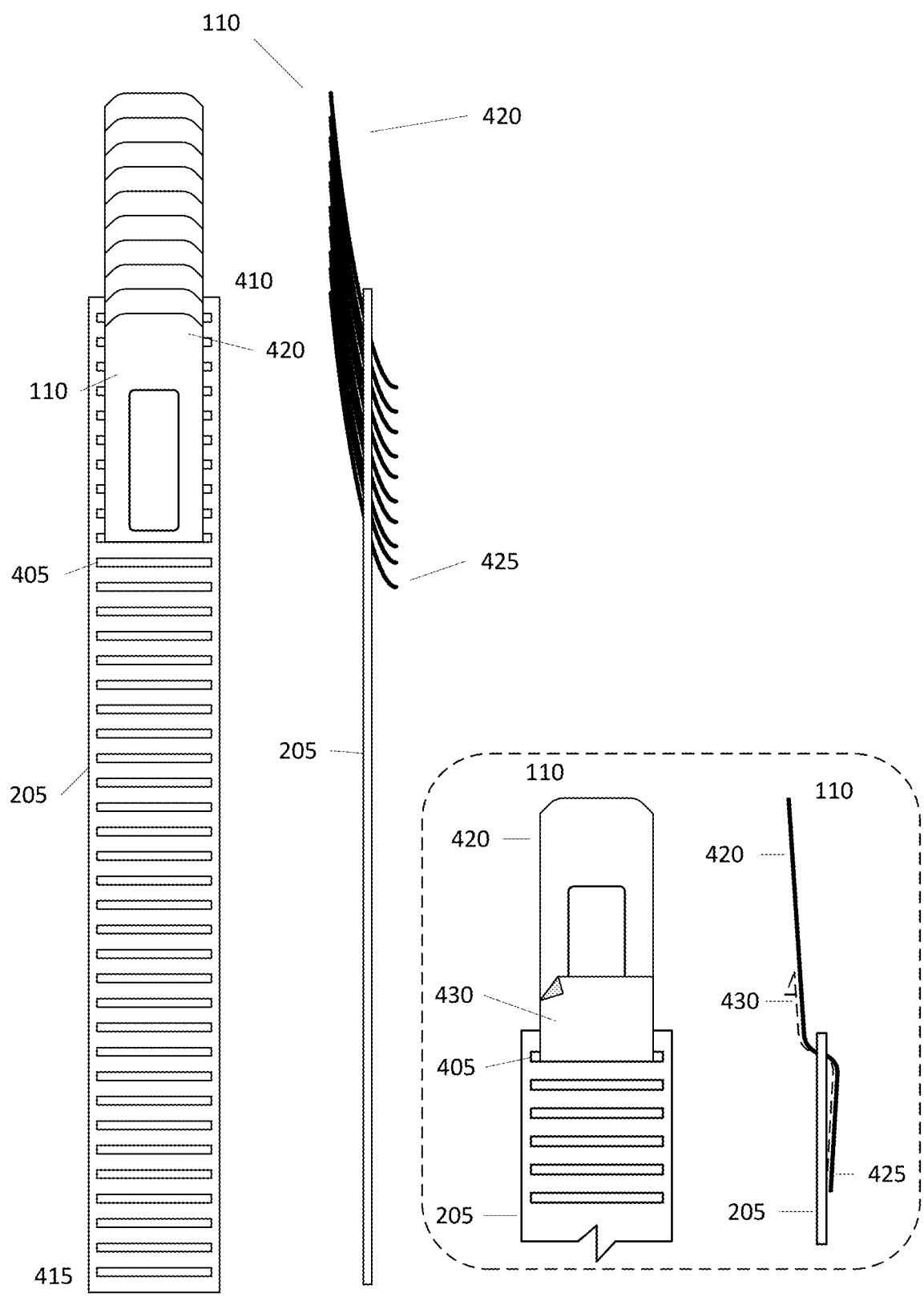
FIG. 4 illustrates perspective views and a detail view of an exemplary bandage carriage with bandages attached thereto, in accordance with some embodiments of the present disclosure.

FIG. 4 illustrates an exemplary bandage carriage 205. As depicted, each bandage 110 comprises a first end 420 and a second end 425. In some embodiments, second end 425 may be attached to carriage 205. In other embodiments, second end 425 may comprise an adhesive backer that may be attached to carriage 205. Although carriage 205 may be depicted and described as having a plurality of bandage slots 405 that are uniform in size, shape, and orientation, any size, shape, or orientation may be implemented without departing from the contemplated embodiments. Other orientations are disclosed herein, for example in FIG. 5. FIG. 4 further illustrates a detail view of an exemplary bandage carriage 205, for example, as shown and described herein. As illustrated, a first bandage (e.g., bandage 110) protrudes through a first bandage slot (e.g., bandage slot 405). As shown, bandage 110 comprises first end 420 and second end 425. Bandage 110 includes adhesive backer 430 (additionally illustrated as a dashed line) attached to second end 425 of bandage 110. Although bandage 110 may comprise adhesive backers on first end 420, second end 245, or both, for simplicity, first end 420 is illustrated without an adhesive backer. In some embodiments, second end 425 of bandage 110 protrudes through bandage slot 405. In some embodiments, adhesive backer 430 is connected to bandage carriage 205, for example, by using adhesive or other suitable techniques for connecting second end 425 and/or adhesive backer 430 to bandage carriage 205, the implementation of which will be readily apparent to one skilled in the art.

Figure 5:
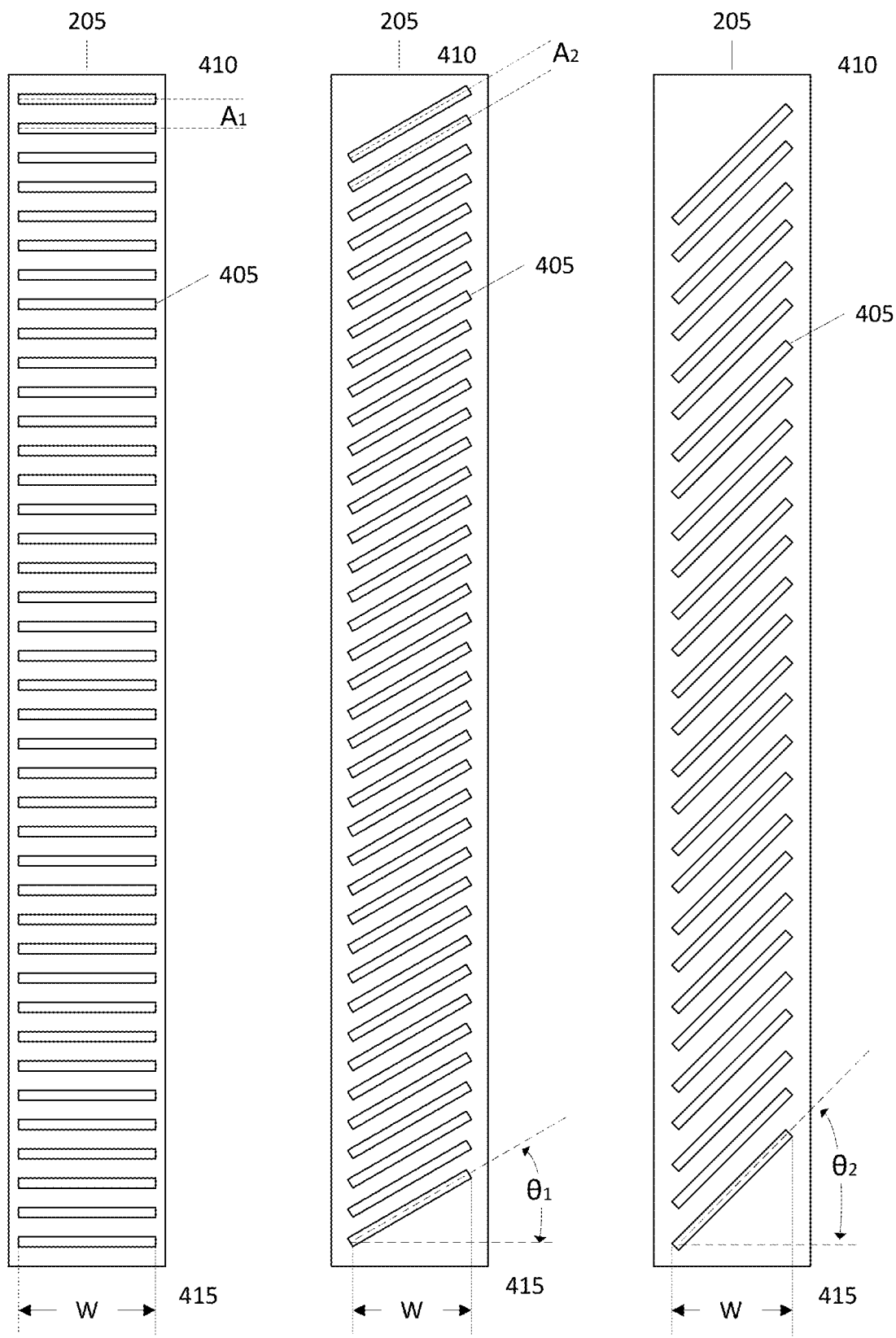
FIG. 5 illustrates perspective views of an exemplary bandage carriage, in accordance with some embodiments of the present disclosure.

In another exemplary embodiment of the present disclosure and with reference to FIG. 5, carriage 205 comprises a plurality of bandage slots 405 extending through the carriage 205. As disclosed herein, the second end 425 of each bandage may protrude through a bandage slot 405. In some embodiments, each bandage of the plurality of bandages 110 comprises an adhesive backer covering the adhesive portion of the bandages 110. In some embodiments, each bandage comprises two adhesive backers, each covering the adhesive portion on the first end 420 of each bandage and the second end 425 of each bandage.

The plurality of bandage slots 405 may be oriented in different configurations. Although bandage slots 405 may be illustrated and described as being a generally rectangular shape, bandage slots 405 may comprise any size and shape suitable to implement the embodiments contemplated herein. Bandage slots 405 may further comprise a width W sufficient to allow a portion of the bandages 110 to protrude therethrough (e.g., the first end 420). FIG. 5 illustrates three different exemplary embodiments of the bandage carriage 205. In some embodiments, the carriage 205 may be formed by joining a first end of the carriage 410 to a second end of the carriage 415. In this way, the carriage 205 may be constructed from a single rectangular piece that has its first end 410 and second end 415 joined together. As illustrated, bandage slots 405 may be oriented in different ways. For example, bandage slots 405 may be oriented such that they are approximately 45 degrees from horizontal (as depicted). In such an example, $\Theta_2$ may be approximately 45 degrees. In another embodiment, bandage slots 405 may be oriented such that they are approximately 30 degrees from horizontal (as depicted). In such an embodiment, $\Theta_1$ may be approximately 30 degrees. In another embodiment, bandage slots 405 may be oriented such that they are approximately horizontal, i.e., $\Theta$ is approximately equal to zero degrees. Although bandage slots 405 may be illustrated and described as being between zero and 45 degrees from horizontal, any orientation may be implemented without departing form the contemplated embodiments, i.e., $\Theta$ can be any angle from 0 to 360. Additionally, although bandage slots 405 are shown and described as being uniform, i.e., all bandage slots 405 are oriented in the same manner, the bandage slots' 405 orientation may not be uniform. In such an embodiment, each bandage slot 405 may be oriented differently from the other bandage slots 405 of the bandage carriage 205.

Figure 6:
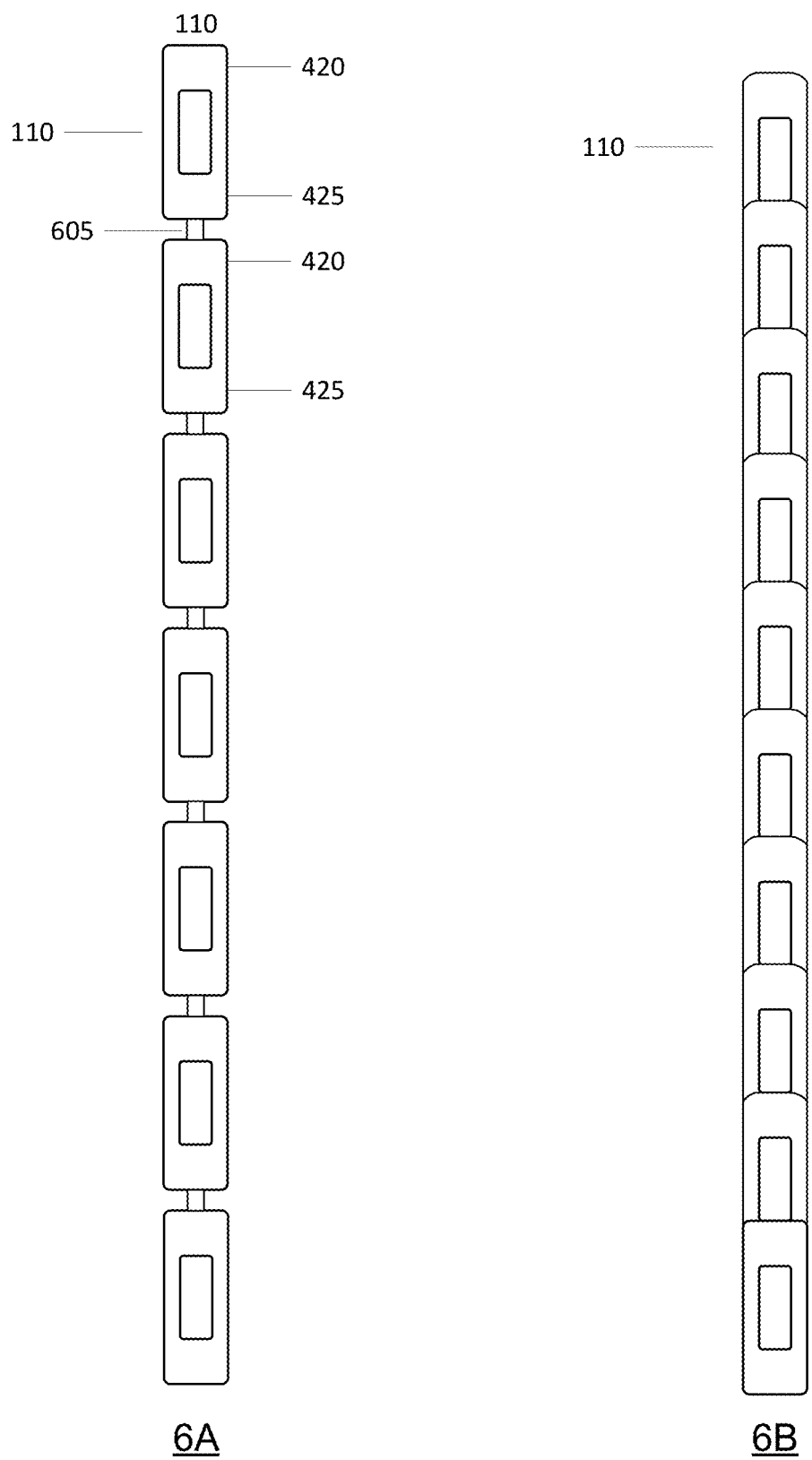
FIG. 6 illustrates perspective views of exemplary bandages, in accordance with some embodiments of the present disclosure.
Figure 7:
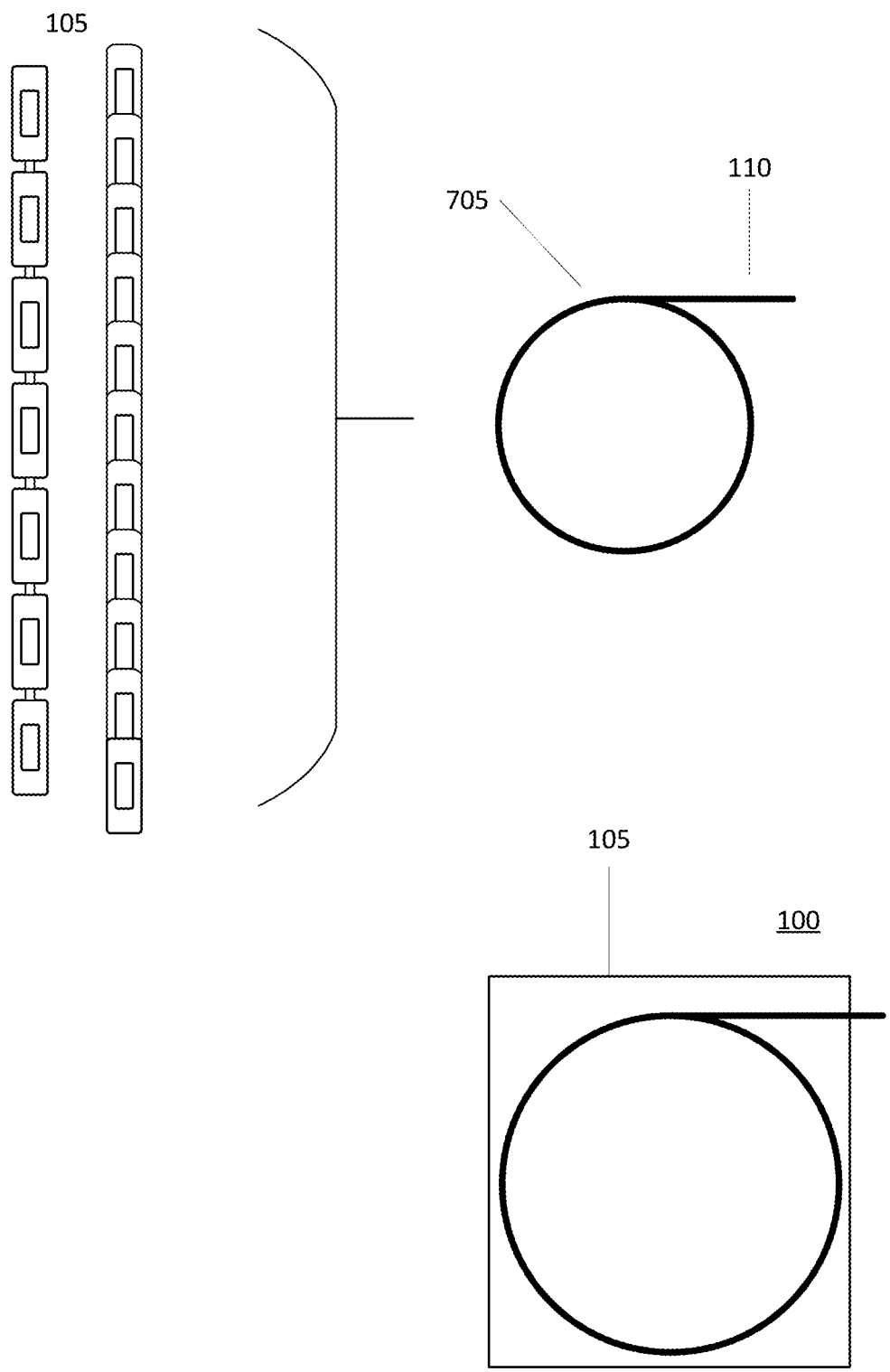
FIG. 7 illustrates perspective views of exemplary bandages formed into a spool, in accordance with some embodiments of the present disclosure.

FIGS. 6 and 7 depict exemplary embodiments of the disclosure wherein the bandage carriage 205 is not used and instead, bandages 110 are configured in a way that obviates the need for a carriage 205.

In another exemplary embodiment of the present disclosure and with reference to FIG. 6, bandages 110 may be joined together. In such an embodiment, each bandage 110 of the plurality of bandages may comprise a first end 420 and a second end 425. Bandages 110 may be joined together in such a way that creates a chain of bandages. As depicted in FIG. 6A, bandages 110 maybe joined together by connector 605. In some embodiments, connector 605 joins the second end 425 of a first bandage to the first end 420 of a subsequent bandage. In this way, the plurality of bandages 110 may be joined together. In some embodiments, connector 605 is attached to the adhesive backers of the first and second bandages of the plurality of bandages 110.

In another exemplary embodiment and as illustrated in FIG. 6B, bandages 110 are connected to one another. In such an embodiment, connecting the plurality of bandages together is achieved without connecter 605.

In another exemplary embodiment of the present disclosure and with reference to FIG. 7, a plurality of bandages 110 that have been joined together, for example as discussed herein with respect to FIG. 6, may be formed into a spool of bandages 705. The spool of bandages 705 may be located in the interior of bandage dispensing device 100. In such an embodiment, bandage carriage 205 may not implemented. However, although the spool of bandages 705 may described without implementing bandage carriage 205, bandage carriage 205 may be used in conjunction with the spool of bandages 705 without departing from the contemplated embodiments.

Figure 8:
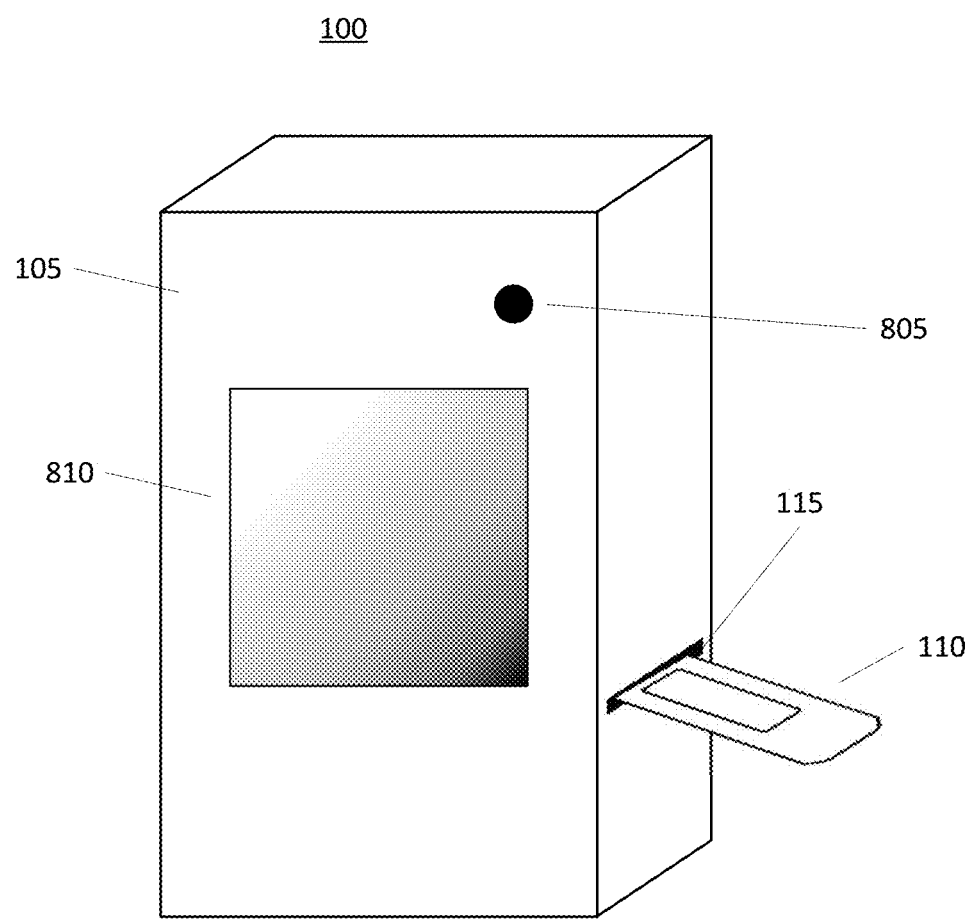
FIG. 8 illustrates an isometric view of an exemplary bandage dispensing device, in accordance with some embodiments of the present disclosure.
Figure 9:
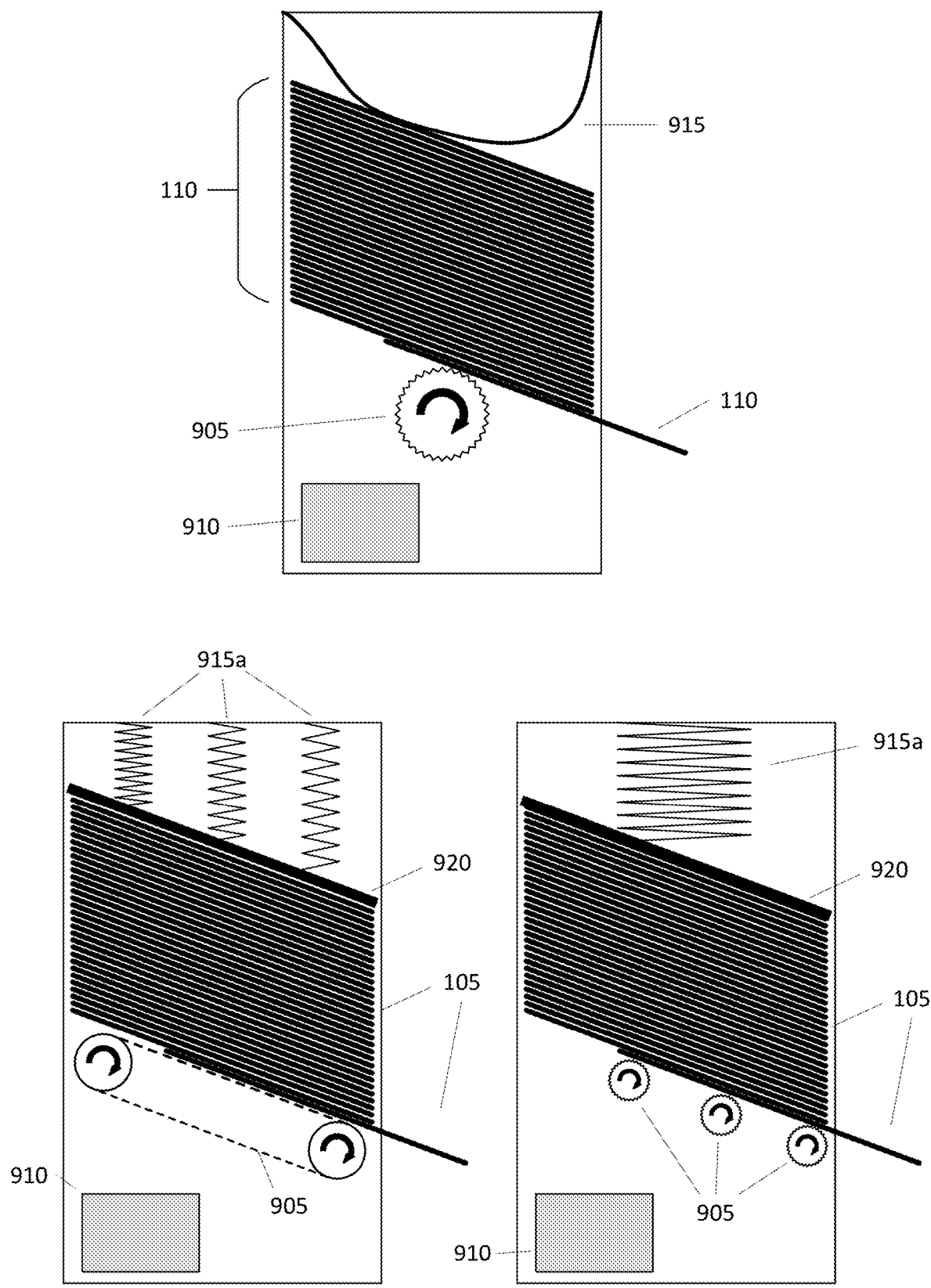
FIG. 9 illustrates perspective views of an exemplary bandage dispensing device, in accordance with some embodiments of the present disclosure.

In another exemplary embodiment of the present disclosure and with reference to FIGS. 8 and 9, bandage dispensing device 100 comprises an exterior 105, a dispensing port 115 through which bandages 110 may be dispensed. Bandage dispensing device 100 may comprise switch 805 and display 810. Switch 805 may be embodied by any device sufficient to interact with bandage dispensing device 100. For example, switch 805 may be embodied by any device or mechanism that is suitable to interact with bandage dispensing device 100, including a pushbutton switch, a throw switch, a selector switch, a joystick switch, a limit switch, or a pressure switch. In some embodiments, switch 805 may comprise an indicator configured to indicate any information related to the operation or functionality of bandage dispensing device 100. For example, switch 805 may comprise a light comprising a single color or multiple colors. In some embodiments, bandage dispensing device 100 may comprise display 810 configured to display any information relating to the functionality or features of bandage dispensing device 100. For example, display 810 may be configured as a transparent window that allows the user to view the number of bandages that are contained within bandage dispensing device 100. In other embodiments, display 810 may be embodied by an electronic display. Nonlimiting exemplary types of displays that may be implemented include liquid crystal (LCD) displays, light-emitting diode (LED) displays, light-emitting diode (LED) backlit LCD displays, and organic light emitting diode (OLED) displays. In other embodiments, display 805 may be digital display capable of displaying, for example, the number of bandages remaining, the power level of power source, the size and shape of the bandages contained within bandage dispensing device 100, or any other information pertaining to the features or functionality of bandage dispensing device 100. In other embodiments, display 810 may be interactive. In such an embodiment, display 810 may comprise, for example, a touch screen allowing the user to interact with bandage dispensing device 100.

FIG. 9 illustrates the interior of an exemplary bandage dispensing device 100, for example as depicted in FIG. 8, according to embodiments disclosed herein. In some embodiments, bandage dispensing device 100 comprises spring 915. Spring 915 may be embodied by device suitable for applying a force, for example, a compression spring, an extension spring, a torsion spring, or a constant force spring, and may further include a helical spring, a disk spring, or a leaf spring. Bandage dispensing device 100 may further comprise conveyor 905. Conveyor 905 may be embodied by any mechanism or device that is suitable for moving bandages 105 to dispensing port 115. Although certain types of conveyors are depicted and described, any type of conveyor may be implemented without departing from the contemplated embodiments. Exemplary types of conveyors that may be implemented include wheel conveyors, cable conveyors, chain conveyors, belt conveyors, pneumatic conveyors, aero-mechanical conveyors, and screw or auger conveyors. Conveyor 905 may comprise high friction surfaces sufficient to interact with bandages 110 in such a way that conveyor 905 is capable of moving bandages 110 as disclosed herein. Bandage dispensing device 100 may also comprise control circuitry 910 that may include computer readable memory and a power source suitable for implementing the functions and features described herein. In some embodiments, conveyor 905 is manually actuated. In such an embodiment, the bandage dispensing device comprises a manual actuator (e.g., switch 805) that is mechanically connected to conveyor 905 such that when actuated, conveyor 905 conveys bandage 110 to dispensing port 115. In this way, embodiments comprising conveyor 905 may be implemented without a power source.

In operation, a user may interact with bandage dispensing device 100 to dispense bandage 110, by for example interacting with switch 805 or interactive display 810. In an embodiment, a plurality of bandages 110 are positioned in bandage dispensing device 100 such that spring 915 applies a force thereto, causing the plurality of bandages 110 be pressed against conveyor 905. In some embodiments, spring 915 applies a force to follower 920 that in turn, distributes the force evenly across bandage 110. A user interacts with bandage dispensing device 100 by, for example, interacting with switch 805 and/or display 810, which generates a signal that is sent to control circuitry 910. Control circuitry 110 causes conveyor 905 to activate, which in turn causes bandage 110 to be passed to and though dispensing port 115 to an amount sufficient for the user to grasp and remove bandage 110 from bandage dispensing device 100. In some embodiments, bandage dispensing device 100 comprises sensors capable of detecting the size, shape, quantity, location, orientation, type, and/or status of bandages 110, or any other information relating to bandage dispensing device 100. In such an embodiment, control circuitry 910 may cause information corresponding to that gathered by the sensors and display it on display 810.

Figure 10:
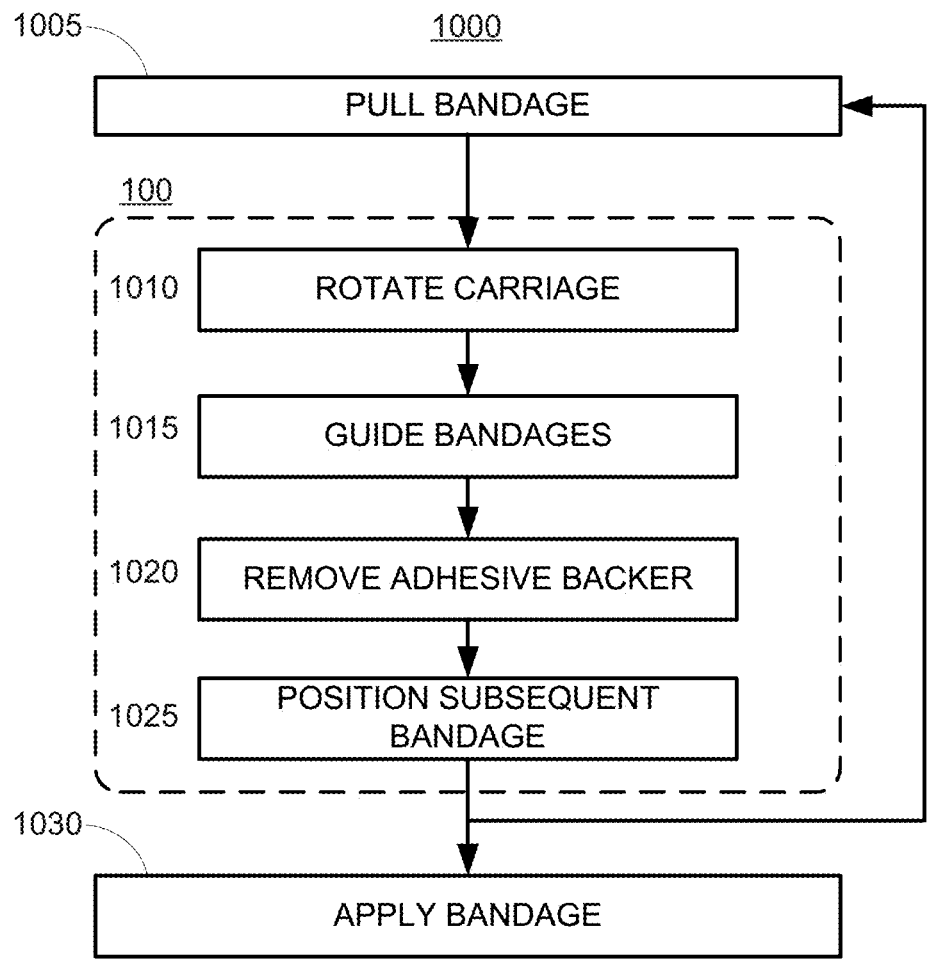
FIG. 10 is a flowchart illustrating an exemplary method of dispensing bandages, in accordance with some embodiments of the present disclosure.

FIG. 10 illustrates an exemplary method for dispensing bandages 110, according to some embodiments of the present disclosure. At step 1005, a user may pull bandage 110 by, for example, grasping first end 420 of bandage 110. At step 1010, the carriage is rotated. In an embodiment, the user pulling on bandage 110 causes the carriage to rotate due to the geometry and orientation of the carriage 205, the bandage 110, and the direction the user pulls bandage 110. In some embodiments where carriage 205 is not implemented (for example, in an embodiment described with respect to FIGS. 6 and 7), stem 1010 may be omitted without departing from the contemplated embodiments. At step 1015, guide 210 keeps the plurality of bandages 110 from being caught or tangled in various areas within bandage dispensing device 100. At step 1015, the plurality of bandages 110 are guided towards dispensing port 115. This may be accomplished as a result of the rotation of carriage 205 rotating (by, for example, the user pulling on a bandage 110) and the plurality of bandages 110 attached thereto. At step 1020, the adhesive backer of bandage 110 is removed as the user continues to pull bandage 110. As the user continues to pull bandage 110, the adhesive backer of second end 425 is removed from bandage 110 by virtue of the adhesive backer being attached to carriage 205. Once the force by which user pulls bandage 110 is sufficient to overcome the adhesive force between the adhesive backer and bandage 110, the adhesive backer is release from bandage 110 leaving the adhesive portion of bandage 110 available for application and the adhesive backer remaining attached to carriage 205. At step 1025, the subsequent bandage of the plurality of bandages 110 is positioned, for example, protruding a portion thereof (e.g., first end 420) through dispensing port 115. At step 1030, once bandage 110 is detached from bandage dispensing device 100, the user may apply bandage 110 as necessary. In some embodiments, steps 1010 through 1025 may be accomplished by virtue of the user pulling on the bandage 110 (e.g., as described with respect to step 1005). In other embodiments, steps 1005 through 1030 may be accomplished independently.

The foregoing is merely illustrative of the principles of this disclosure, and various modifications may be made by those skilled in the art without departing from the scope of this disclosure. The embodiments described herein are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:
1. A bandage dispensing device comprising:
an exterior of the bandage dispensing device enclosing an interior of the bandage dispensing device;

a dispensing port;

a bandage carriage comprising a generally circular shape and located within the interior of the bandage dispensing device; and a first bandage of a plurality of bandages;

wherein the bandage carriage comprises an interior and an exterior;

wherein the bandage carriage comprises a plurality of bandage slots, each extending from the exterior of the bandage carriage to the interior of the bandage carriage; and wherein a portion of the first bandage extends through a first bandage slot of the plurality of bandage slots such that the portion of the first bandage extends into the interior of the bandage carriage and the remainder of the first bandage extends to the exterior of the bandage carriage.

2. The bandage dispensing device of claim 1, wherein each bandage of the plurality of bandages comprises an adhesive backer and wherein the adhesive backer is connected to the bandage carriage.

3. The bandage dispensing device of claim 1, further comprising:

a guide located in the interior;

wherein the guide circumscribes a portion of the interior of the bandage dispensing device corresponding to a circumference of the bandage carriage.

4. A method of dispensing bandages comprising:

pulling a first end of a first bandage of a plurality of bandages, wherein the first end of the first bandage protrudes through a dispensing port;

wherein a second end of the first bandage of the plurality of bandages is connected to a bandage carriage located in an interior of a bandage dispensing device;

wherein the bandage carriage is configured in a generally circular shape defining an interior and an exterior;

wherein the bandage carriage comprises a plurality of bandage slots, each extending from the exterior of the bandage carriage to the interior of the bandage carriage; and wherein the second end of the first bandage extends through a first bandage slot of the plurality of bandage slots such that the second end of the first bandage extends into the interior of the bandage carriage and the remainder of the first bandage extends to the exterior of the carriage.

5. The method of claim 4, wherein the second end of the first bandage of the plurality of bandages further comprises an adhesive backer attached to the carriage.

6. A bandage carriage comprising:

a plurality of bandage slots;

wherein the bandage carriage comprises a generally circular shape defining an interior and an exterior;

wherein each bandage slot of the plurality of bandage slots extends from the exterior of the bandage carriage to the interior of the bandage carriage;

wherein a portion of the bandage extends through a first bandage slot of the plurality of bandage slots such that the portion of the bandage extends into the interior of the bandage carriage and the remainder of the bandage extends to the exterior of the bandage carriage.

7. The bandage carriage of claim 6, wherein each bandage slot of the plurality of bandage slots comprises a generally rectangular shape.

\* \* \* \* \*